(12) United States Patent
Liongosari et al.

(10) Patent No.: US 10,507,774 B2
(45) Date of Patent: Dec. 17, 2019

(54) COMPONENT CONFIGURATION BASED ON SENSOR DATA

(71) Applicant: Accenture Global Solutions Limited, Dublin (IE)

(72) Inventors: Edy S. Liongosari, San Jose, CA (US); Alex M. Kass, Palo Alto, CA (US); Niclas Almquist, Enebyberg (SE)

(73) Assignee: Accenture Global Solutions Limited, Dublin (IE)

( * ) Notice: Subject to any disclaimer, the term of this patent is extended or adjusted under 35 U.S.C. 154(b) by 100 days.

(21) Appl. No.: 15/679,680

(22) Filed: Aug. 17, 2017

(65) Prior Publication Data
US 2019/0054873 A1 Feb. 21, 2019

(51) Int. Cl.
*B60R 16/037* (2006.01)
*B60R 21/015* (2006.01)
(Continued)

(52) U.S. Cl.
CPC .......... *B60R 16/037* (2013.01); *B60N 2/0244* (2013.01); *B60R 21/01552* (2014.10);
(Continued)

(58) Field of Classification Search
CPC ............ B60H 1/00742; B60H 1/00792; B60H 1/00764; B60H 1/00492; B60R 16/037;
(Continued)

(56) References Cited

U.S. PATENT DOCUMENTS 4,797,924 A * 1/1989 Schnars .............. B60R 16/0373
704/275
4,907,153 A * 3/1990 Brodsky .............. B60N 2/0244
296/65.12
(Continued)

FOREIGN PATENT DOCUMENTS

WO 2015/127193 8/2015
WO 2016/115230 7/2016

OTHER PUBLICATIONS

European Search Report and Written Opinion in European Application No. 18186681.5, dated Dec. 17, 2018, 14 pages.

*Primary Examiner* — Hunter B Lonsberry
*Assistant Examiner* — Luis A Martinez Borrero
(74) *Attorney, Agent, or Firm* — Fish & Richardson P.C.

(57) ABSTRACT

Techniques are described for component configuration based on sensor data. Sensor data is collected by sensors in, or proximal to, a system under diagnosis (e.g., a vehicle), the sensor data describing the use of component(s) of the system by individual(s). The sensor data is analyzed (e.g., in real time) to determine an updated configuration for component(s) (e.g., an adjustment to the seat back, lumbar support of a car seat, etc.). The updated configuration may be communicated to the individual as a recommended configuration. In some implementations, the updated configuration may be communicated directly to the component which, on receiving and processing the configuration update, sends signals to various actuators to move the subcomponents of the component into the updated configuration. In (Continued)

some implementations, the sensor data is used to train, through machine learning, a model that provides configuration update(s) for component(s) based on the input sensor data.

21 Claims, 5 Drawing Sheets

(51) Int. Cl.
*B60N 2/02* (2006.01)
*B60W 40/08* (2012.01)
*B60W 40/09* (2012.01)
*B60W 50/08* (2012.01)
*G05B 19/042* (2006.01)
*G06F 19/00* (2018.01)
*G06F 17/50* (2006.01)

(52) U.S. Cl.
CPC .......... *B60W 40/08* (2013.01); *B60W 40/09* (2013.01); *B60W 50/085* (2013.01); *G05B 19/0426* (2013.01); *G06F 17/50* (2013.01); *G06F 19/36* (2013.01)

(58) Field of Classification Search
CPC ............ B60R 16/03; B60R 16/0373; B60R 21/01552; B60R 16/02; B60R 21/0154; G16H 20/30; G05D 1/0088; G05D 2201/0213
See application file for complete search history.

(56) References Cited

U.S. PATENT DOCUMENTS

| | | | | |
|---|---|---|---|---|
| 5,319,248 A * | 6/1994 | Endou | .................. | G05B 19/238 307/10.1 |
| 6,064,932 A * | 5/2000 | François | .............. | B60N 2/0228 340/438 |
| 6,240,347 B1 * | 5/2001 | Everhart | ................ | B60K 35/00 701/36 |
| 6,255,790 B1 * | 7/2001 | Popp | ...................... | B60N 2/002 307/10.1 |
| 7,239,096 B2 * | 7/2007 | Hancock | .............. | B60N 2/0228 318/50 |
| 10,007,478 B2 * | 6/2018 | Wang | .................. | B60N 2/0232 |
| 2003/0209893 A1 * | 11/2003 | Breed | ..................... | B60J 10/00 280/735 |
| 2004/0143440 A1 * | 7/2004 | Prasad | ............... | B60R 16/0373 704/270 |
| 2006/0155547 A1 * | 7/2006 | Browne | .................. | G10L 15/26 704/275 |
| 2010/0318266 A1 * | 12/2010 | Schaaf | ................... | B60K 35/00 701/49 |
| 2013/0013157 A1 * | 1/2013 | Kim | ...................... | B60R 16/037 701/49 |
| 2014/0088793 A1 * | 3/2014 | Morgan | ............... | B60R 16/037 701/2 |
| 2014/0265479 A1 * | 9/2014 | Bennett | .................. | B60N 2/919 297/217.4 |
| 2015/0084985 A1 * | 3/2015 | Baudu | ................. | B60N 2/0244 345/629 |
| 2015/0145296 A1 | 5/2015 | Hotary et al. | | |
| 2015/0253747 A1 | 9/2015 | Chun et al. | | |
| 2016/0379631 A1 * | 12/2016 | Wang | .................. | B60N 2/0232 704/275 |
| 2018/0134116 A1 * | 5/2018 | Chen | .................. | B60H 1/00742 |
| 2018/0148007 A1 * | 5/2018 | Gage | .................. | B60R 16/037 |
| 2018/0202678 A1 * | 7/2018 | Ahuja | ................... | G05B 15/02 |
| 2018/0202686 A1 * | 7/2018 | Ahuja | ................... | G05B 15/02 |
| 2018/0229674 A1 * | 8/2018 | Heinrich | ............. | B60R 16/0231 |
| 2019/0077346 A1 * | 3/2019 | Pankow | ................ | B60R 16/037 |

* cited by examiner

COMPONENT CONFIGURATION BASED ON SENSOR DATA

BACKGROUND

During a typical day, an individual may interact with a variety of objects that are at least partly adjustable by the individual. For example, various components of a vehicle, such as a seat, steering wheel, entertainment system, engine components, and so forth may be adjusted by the individual in an attempt to enhance comfort, ease of use, efficiency, and/or achieve other purposes. In many instances, individuals may not have the patience or knowledge to know which particular adjustments would be most advantageous for the various components in various scenarios. Accordingly, many adjustable components may be used in a way that does not take advantage of their full potential for positive user experience and functionality.

SUMMARY

Implementations of the present disclosure are generally directed to determining a component configuration and/or design based at least partly on sensor data collected during use of the component by one or more users. More particularly, implementations of the present disclosure are directed to collecting sensor data that describe movements, actions, physiological state, and/or other characteristics of user(s) while using the component, and analyzing the sensor data to determine an updated configuration (e.g., position, orientation, etc.) for the component as a recommendation to the user or as an automatically activated configuration for the user.

In general, innovative aspects of the subject matter described in this specification can be embodied in methods that include actions of: receiving sensor data describing at least one action that is performed by a user while using a component, the sensor data at least partly generated by at least one sensor device in proximity to the component; analyzing the sensor data to determine a satisfaction metric that indicates a level of satisfaction of the user with a current configuration of the component; based on the sensor data and the satisfaction metric, determining an updated configuration that is predicted to increase the level of satisfaction of the user with the component; and communicating the updated configuration to one or more of the component and the user.

These and other implementations can each optionally include one or more of the following innovative features: the at least one action includes at least one movement of the user; analyzing the sensor data includes inferring, based on the at least one movement, that the user is experiencing physical discomfort while using the component; the updated configuration is predicted to decrease a rate of occurrence of the at least one movement and alleviate the physical discomfort of the user using the component; the at least one action includes at least one adjustment, by the user, to the current configuration of the component; communicating the updated configuration instructs the component to move into the updated configuration; communicating the updated configuration causes the updated configuration to be presented as a recommendation to the user; the at least one sensor device is incorporated into the component; the sensor data further includes biometric data that describes at least one physiological characteristic of the user, the biometric data generated by at least one biometric sensor device in proximity to the user; the at least one physiological characteristic of the user includes one or more of heart rate, pulse, blood pressure, perspiration level, galvanic skin response, body temperature, and neural activity; the component is an adjustable seat in a vehicle; the current configuration includes one or more of a position and an orientation for each of a plurality of subcomponents of the adjustable seat; one or more of analyzing the sensor data, determining the updated configuration, and communicating the updated configuration are performed in real time with respect to receiving the sensor data; the updated configuration is communicated based on determining that the satisfaction metric is below a predetermined threshold level; the sensor data includes an explicit indication, by the user, that the user is dissatisfied with the current configuration; the component includes a plurality of subcomponents that each includes at least one respective sensor device that generates a portion of the sensor data by measuring at least one characteristic of the respective subcomponent; the respective portion of the sensor data is provided to the component from each of the plurality of subcomponents; the plurality of subcomponents is arranged in a hierarchy of at least two levels; the updated configuration is further based on at least one characteristic of the user, including one or more of a height or a weight of the user; the at least one characteristic is measured by the at least one sensor device; determining the updated configuration employs a model that is developed, using a machine learning algorithm, to output the updated configuration that optimizes the level of satisfaction for the user; and/or the sensor data includes one or more of a glance of the user toward the component, a spoken statement of the user regarding the component, and a gesture of the user toward the component.

In general, innovative aspects of the subject matter described in this specification can be embodied in methods that include operations of: receiving, from each of a plurality of instances of a component, sensor data describing at least one action that is performed by a respective user while using the respective instance of the component, wherein the sensor data is at least partly generated by at least one sensor device in proximity to the respective instance of the component; aggregating the sensor data from the plurality of instances of the component to generate aggregate sensor data; based at least partly on the aggregate sensor data, generating design information that describes at least one modification to the component; and providing the design information for output through a user interface.

These and other implementations can each optionally include one or more of the following innovative features: the operations further include analyzing the aggregate sensor data to infer, based on the at least one action of at least one user, that the at least one user is experiencing physical discomfort while using the component; the operations further include determining the at least one modification to reduce the physical discomfort; the at least one action includes at least one adjustment, by the respective user, to a configuration of the component; the at least one sensor device is incorporated into the component; the sensor data further includes biometric data that describes at least one physiological characteristic of the user, the biometric data generated by at least one biometric sensor device in proximity to the user; the at least one physiological characteristic of the user includes one or more of heart rate, pulse, blood pressure, perspiration level, galvanic skin response, body temperature, and neural activity; the component is an adjustable seat in a vehicle; the at least one action includes adjusting one or more of a position and an orientation for each of one or more subcomponents of the adjustable seat; the sensor data includes an explicit indication, by the respective user, that the respective user is dissatisfied with a configuration of the component; the component includes a plurality of subcomponents that each includes at least one respective sensor device that generates a portion of the sensor data by measuring at least one characteristic of the respective subcomponent; the respective portion of the sensor data is provided to the component from each of the plurality of subcomponents; the plurality of subcomponents is arranged in a hierarchy of at least two levels; generating the at least one modification to the component includes identifying at least one portion of the component that is associated with the at least one action performed by one or more users, as indicated in the aggregate sensor data, presenting a design view of the component in the user interface with a graphical indication of the at least one portion of the component, and receiving, through the user interface, the at least one modification to the at least one portion of the component; and/or generating the at least one modification to the component includes identifying at least one portion of the component that is associated with the at least one action performed by one or more users, inferring that the at least one action indicates a physical discomfort experienced by the one or more users while using the component, and determining the at least one modification to the at least one portion of the component to reduce the physical discomfort.

Other implementations of any of the above aspects include corresponding systems, apparatus, and computer programs that are configured to perform the actions of the methods, encoded on computer storage devices. The present disclosure also provides a computer-readable storage medium coupled to one or more processors and having instructions stored thereon which, when executed by the one or more processors, cause the one or more processors to perform operations in accordance with implementations of the methods provided herein. The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

Implementations of the present disclosure provide one or more of the following technical advantages and improvements over traditional systems. Through use of sensor data that is collected from a component being used by one or more users, and by analyzing the sensor data to determine configuration updates and/or design updates for the component, implementations provide for the generation of configuration and/or design updates that are objectively determined based on the measured responses of users using the component. Such updates may be more accurate and more effective in reducing user discomfort, compared to updates that are created using traditional, ad hoc design paradigms. Accordingly, implementations avoid the need for repeated, iterative redesigns and/or configuration updates which would consume network bandwidth, processing capacity, active memory, storage space, and/or other computing resources. Moreover, implementations provide various technical advantages with respect to the dynamic determination of design updates, including one or more of the following: determining whether a particular component should be mandatory or optional, e.g., in a vehicle; determining whether a component should be fixed in a particular position (e.g., non-adjustable), or whether it should be adjustable (e.g., movable) by the user; and/or determining under what circumstances a component is being used (e.g., the user is alone in the vehicle in a heavy traffic jam, the component is used at night only, etc.), and determining design updates based at least in part on such use. The design updates may also include determining an optimal initial setup for a component, such as an initial and/or default configuration of the component (e.g., should the default on or off, an initial setting of a car seat, etc.).

It is appreciated that aspects and features in accordance with the present disclosure can include any combination of the aspects and features described herein. That is, aspects and features in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DETAILED DESCRIPTION

Figure 1:
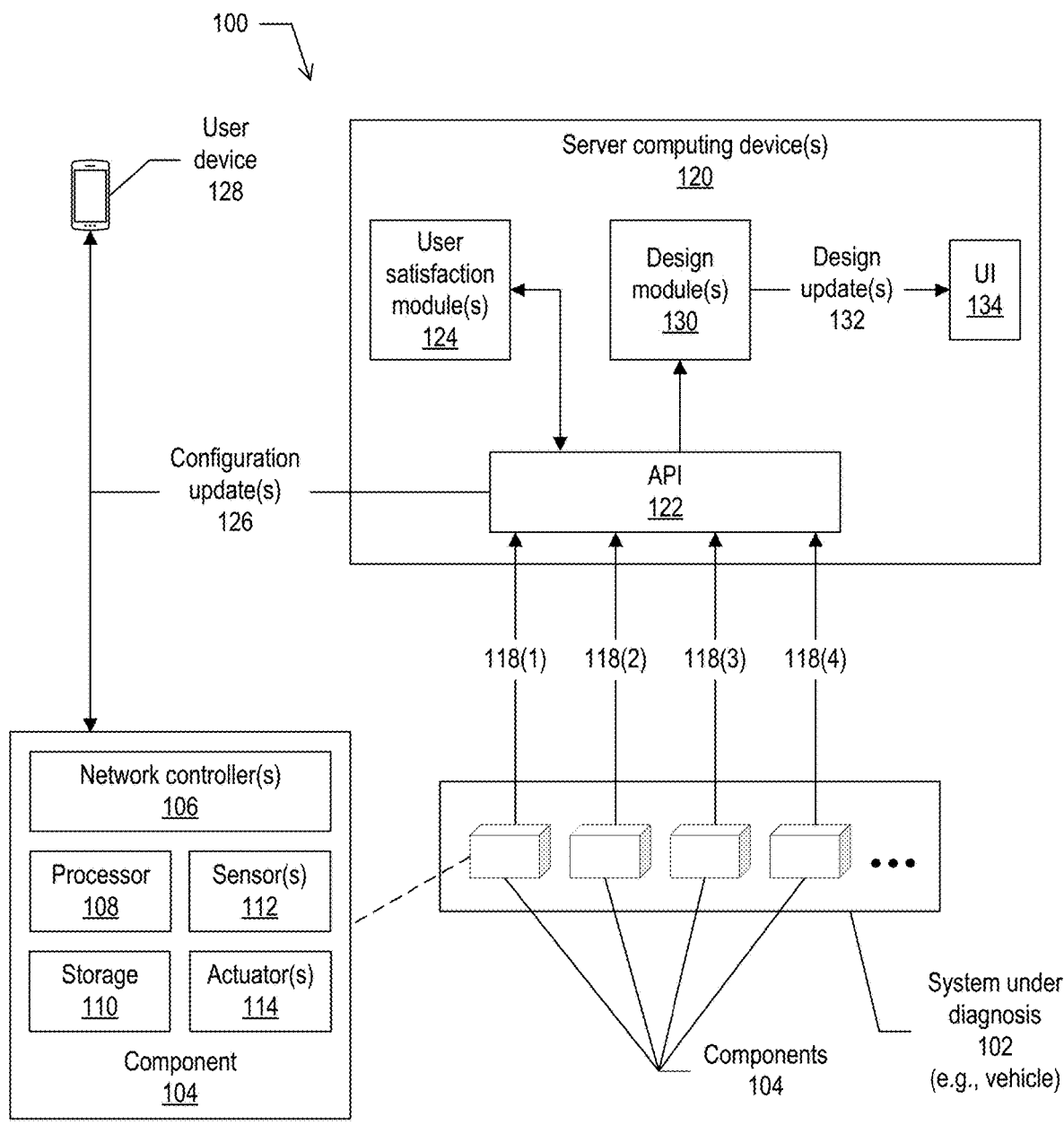
FIG. 1 depicts an example system for component configuration and/or design based on collected sensor data, according to implementations of the present disclosure.

Implementations of the present disclosure are directed to systems, devices, methods, and computer-readable media for component configuration and/or design based on collected sensor data. Various types of sensor data are collected by sensors (also described as sensor devices) in proximity to a user who is using a component. In some instances, the sensors may be incorporated into the component, or may be proximal to the component and/or arranged to gather data regarding the user's use of the component. The sensors may include motion sensors that detect various motions (e.g., intentional actions and/or unintentional, subconscious movements) made by the user with respect to the component. Sensors may also collect other types of sensor data, including biometric data that describes current physiological characteristics of the user (e.g., body temperature, heart rate, perspiration, etc.). The sensor data may be communicated to server device(s) that analyze the sensor data and, based at least partly on the sensor data, determine a current level of satisfaction of the user with the configuration of the component. Sensor data may be received and analyzed for any suitable number of components being used by individuals.

In some implementations, the sensor data may be analyzed (e.g., in real time) to determine an updated configuration for the component, such as an adjustment to the seat back, lumbar support, seat position, and/or head rest of an adjustable car seat. The updated configuration may be communicated to the user as a recommended configuration that may alleviate the user's physical discomfort. In some implementations, the updated configuration may be communicated directly to the component which, as a smart component, may receive and process the configuration update and send a signal to various actuators to move the subcomponents of the component into the updated configuration. In some implementations, the sensor data may be provided as input to a model that is trained or otherwise developed using a suitable machine learning (ML) technique. The model may output one or more configuration updates for the component based on the input sensor data, and such configuration update(s) may be recommended to the user and/or communicated to the component as described above.

In some implementations, the sensor data from various instances of the component (e.g., a same or similar car seat installed in multiple vehicles used by different individuals) may be aggregated and analyzed, as aggregate sensor data, to determine one or more updates to the design of the component. In some implementations, the aggregate sensor data may be analyzed to identify portions and/or subcomponents of the component that are frequently associated with movements by users (e.g., fidgeting, adjustments), indicating that a proportion of the users of the component are uncomfortable with the particular design of the portion and/or subcomponent. These identified portion(s) or sub-component(s) may be presented as an overlay or other graphic enhancement to a design view of the component, rendered in a computer-aided design (CAD) system, computer-aided manufacturing (CAM) system, or some other suitable design tool. A designer may then use the indicated portion(s) and/or subcomponent(s) to determine one or more modifications to the component, specified through the design view, to attempt to reduce the physical discomfort or otherwise improve the usability or operations of the component. In some implementations, the aggregate sensor data may be provided as input to a model that is trained or otherwise developed using a suitable ML technique. The model may output one or more design modifications for the component based on the input aggregate sensor data, and such modification(s) may be provided for presentation in a design view or some other user interface (UI).

In some implementations, the components include "smart" automobile components, such as a smart car seat, a smart steering wheel, and so forth, which are configurable through user operations and/or through signals sent from an on-board or external computing system. Through an analysis of on-board (e.g., in-vehicle) sensor measurements and/or other data, an estimate is made of whether a user is currently satisfied with the component and/or its subcomponents. The level of satisfaction may be estimated, for example, by measuring an amount of subconscious motion (e.g., fidgeting) that a user is exhibiting with respect to the component and/or when the user is using the component. For example, excessive fidgeting in a car seat may indicate that the using is physically uncomfortable or otherwise dissatisfied with the current configuration of the car seat. A level of satisfaction may also be determined by prompting the user to indicate whether they are satisfied, and/or by measuring biometric parameters (e.g., body temperature, heart rate, gaze, etc.) that may indicate the level of satisfaction or dissatisfaction.

An indication of the estimated current satisfaction and a representation of any component configuration may be sent to the server computing device(s) that provide a (e.g., cloud-based) satisfaction improvement service to prepare and return recommendations or commands in real-time for improving the user's satisfaction, e.g., through a proposed adjustment of the component configuration. Additionally, or alternatively, the satisfaction improvement system can use this information in a process, e.g., a generative design process and/or within a design view, for improving future versions of the component and/or its various subcomponent(s).

In some implementations, sensors in the components generate sensor data that indicates a current state of the component and/or the user of the component, and such sensor data is communicated to the server computing device(s) for analysis and determination of configuration update(s) and/or design update(s). The determination of the configuration update(s) and/or design update(s) may be through the execution of one or more models, such as ML-trained model(s), on the server computing device(s). Alternatively, the analysis of the sensor data may be performed, at least partly, on the component itself. In some implementations, components such as car seats, mirrors, navigation systems, brake systems, and so forth, are each implemented as a platform, with its own processing logic, memory, network interfaces, sensors, and actuators, as well as the ability to locally execute the models to determine configuration update(s) and/or design update(s). A model, executing on the component or on the server(s), receive the sensor data as input and, based on the sensor data, determines whether a person is satisfied (e.g., comfortable) with a current configuration of the component. User dissatisfaction with the component configuration can be inferred from various signals, such as movement or fidgeting, excessive use of actuators (e.g., manual adjustment of component position and/or orientation), explicit inputs, deviations from normal use, temperature, moving the component to an extreme position, and/or other indicators. In some implementations, the model outputs a satisfaction metric that indices an estimated level of satisfaction of the user with the current configuration of the component. is able to annotate the raw sensor data with the satisfaction indication, and upload this data to a higher level system within the vehicle, to a cloud based comfort management system, or to a manufacturer's design studio. Such data is able to be used to design better versions of the component, or to suggest a different setting that might make the user more comfortable.

Based on the sensor data describing usage of a component by an individual, a model can be trained to automatically detect when a configuration change is to be made to the component. In some instances, the model can determine that a configuration change might be desirable, but that the probability of a positive outcome (e.g., enhanced user experience) is not high enough to merit making the change with confidence that the customer will like it. In those instances, a suggestion may be provided to the individual, through an interface in proximity to the user (e.g., in the vehicle). Such an interface can provide the suggestion using any suitable format, such as a display of textual, graphic, or other information, audio output, touch screen, indicator lights, and so forth. For example, a suggestion may be provided to the user: "In these conditions, you sometimes like to cool the car down a bit, would you like to do so now?" or "Would you like a bit stiffer lumbar support?" The user can either accept or reject a suggestion, and the user's choice may be provided to further refine the model. Such mixed and/or shared control provides further refinement of the model in addition to a positive user experience.

In some implementations, features are provided to enable the sharing of data between users. For example, one user's system might be configured to reflect predictions about their needs or preferences, where such predictions are based on other users. In some implementations, similar components in various vehicles, e.g., a class, category, and/or family of components, may be analyzed to determine design updates. For example, a user may own a vehicle of a particular make and model X, and the user may be on vacation and rent a vehicle of make and model Y. Even if the seats in the two vehicles are different, there may be sufficient component data to map the seat settings from one to another. Accordingly, when the user gets into the rental vehicle, the seat may be initially configured automatically in a way that is likely to satisfy their preference and/or conform to their typical usage patterns from their owned vehicle, e.g., not necessarily set the same way as in the owned vehicle, but set in a way that the system can predict the user is likely to want, based on how the user sets the seat in their owned vehicle and/or based on how other users set the same (or similar) seat in their same (or similar) vehicles.

When a user enters a vehicle for the first time, the system can use an initial sensor data capture to determine an optimal configuration for this type of user (e.g., height, weight, etc.) and set the component parameters accordingly. The initial configuration can be based on the historical collection from many users and/or be based on average parameter settings once the type of user has been determined. The interaction of this initial update and/or setting phase can be supported by a dialogue that is initiated with the user through an interface in the vehicle, e.g., "We recommend to adjust your seat to give you better comfort."

FIG. 1 depicts an example system 100 for component configuration and/or design based on collected sensor data, according to implementations of the present disclosure. As shown in the example of FIG. 1, a system under diagnosis 102 can include any suitable number of components 104. For example, the system under diagnosis 102 may be a vehicle, and the components 104 may include one or more of a car seat, steering wheel, entertainment system, navigation system, engine components, and so forth. In some instances, the system under diagnosis 102 may include a single component 104. For example, the system under diagnosis 102 may be an adjustable chair (e.g., desk chair) that includes the chair itself as a component 104. In general, the system under diagnosis 102 may include any suitable number of components 104.

At least some of the component(s) 104 may be "smart" component(s) that are capable of executing software to perform actions. In such instances, a component 104 includes at least one processor 108 and data storage 110 (e.g., memory). A component 104 can include one or more network controllers 106 for sending and/or receiving communications over one or more networks. The network controller(s) 106 may enable communication over wired and/or wireless networks, and may also be described as network interface(s), network interface controller(s) (NIC(s)), or transceiver(s). A component 104 may include, and/or communicate with, any number of sensor(s) 112, which are also described as sensor device(s). In some instances, a sensor 112 is incorporated into the component 104 itself. Alternatively, a sensor 112 may be external to the component 104 and arranged to visualize the component 104 and/or otherwise collect sensor data 118 regarding a user's use of, or interaction with, the component 104. In some instances, the component 104 may include one or more actuators 114 that are configured to alter the configuration of the component 104, e.g., by moving subcomponent(s) into particular position(s) and/or orientation(s) to achieve a particular configuration of the component 104.

Each of one or more components 104 may generate sensor data 118 through use of the sensor(s) 112 that are included in, or connected to, the component 104. The sensor data 118 may include information regarding a current state of the component 104, such as data describing a current configuration of the component 104. For example, a car seat component may generate sensor data 104 that describes a current position and/or orientation of the seat itself (e.g., relative to the steering wheel), as well as the lumbar support, head rest, thigh support, and/or other configurable subcomponents of the car seat. The sensor data 118 may also include information describing a user's interactions with the component 104 and/or the user's actions with respect to the component 104. For example, the sensor data 118 may describe movements of the user with respect to the component 104, such as subconscious fidgeting or intentional movements performed by the user to adjust the component 104. The sensor data 118 may describe other actions performed by the user with respect to the component 104, such as glances toward the component 104, words spoken regarding the component 104, gestures of the user toward the component 104, and so forth. The sensor data 118 may also describe environmental conditions in proximity to the component 104, such as an ambient temperature, air pressure, wind speed, humidity, ambient light level (e.g., daytime versus nighttime), ambient sounds or sound level, and so forth.

Accordingly, the sensor(s) 112 may include any suitable sensor(s) that are configured to generate the sensor data 118 based on observations and/or measurements of the component 104 and/or the user interacting with the component 104. For example, the sensor(s) 112 may include motion sensors that detect movements of the user (e.g., intentional and/or subconscious movements) with respect to the component 104. The sensor(s) 112 may also include environmental sensors that measure the current air temperature, humidity, air pressure, wind speed, ambient light level, ambient sound level, and/or other environmental conditions.

In some implementations, the sensor data 118 includes biometric data that describes current physiological characteristics of the user while using the component 104, such as the user's heart rate, pulse, blood pressure, perspiration level, blood sugar level, galvanic skin response, pupil dilation, respiration, neural activity (e.g., brain wave activity), facial expression or movement, and so forth. In such instances, the sensor(s) 112 may include sensor(s) that are configured to collect such biometric data.

One or more of the components 104 may use their network controller(s) 106 to communicate at least a portion of the sensor data 118, over one or more networks, from the component 104 to one or more server computing devices 120 (also described as server(s)). The server(s) may include any suitable number and type of computing device. In some implementations, the server(s) may provide distributed computing services (e.g., cloud computing service), such as a cloud-based satisfaction improvement service.

In some instances, each component 104 may communicate the sensor data 118 that is generated by its sensor(s) 112. In some instances, one or more components 104 may communicate sensor data 118 to other components, which may send accumulated sensor data 118 of multiple components 104 to the server(s). In some implementations, the components 104 are logically organized in a hierarchical tree arrangement, and the sensor data may propagate upward through the tree until reaching a top-level component 104 that communicates the accumulated sensor data from the hierarchy to the server(s). Such a hierarchy is described further with reference to FIG. 2. The sensor data 118 from one or more components 104 is received through one or more application programming interfaces (APIs) 122 executing on the server(s) 120.

In some implementations, the server computing device(s) 120 execute one or more user satisfaction modules 124. The module(s) 124 receive the sensor data 118 and analyze the sensor data 118 to determine, for a particular component 104, a satisfaction metric that indicates a current level of satisfaction of a user with the component 104. The satisfaction metric may indicate that the user is satisfied (e.g., comfortable) with the current configuration of the component 104, or that the user is unsatisfied (e.g., uncomfortable) with the current configuration of the component 104. In some implementations, the analysis employs a ML-trained model that has been developed to output a satisfaction metric that predicts the level of satisfaction based on input sensor data for the component 104.

Based on the satisfaction metric and the sensor data 118, the module(s) 124 may generate one or more configuration updates 126 to the configuration of the component 104. For example, an inferred discomfort of the user with the current configuration of an adjustable car seat may lead to a configuration update 126 that alters the position and/or orientation of various subcomponents of the car seat, such as adjustments to the head rest, lumbar support, and/or other adjustable subcomponents, and/or a change to the position of the seat as a whole (e.g., moving the seat forward or back relative to the front of the vehicle).

In some implementations, the configuration update(s) 126 are communicated to a user device 128 that is registered to a user of the component 104, such that the configuration update(s) 126 are presented to the user as recommendations for component adjustments that may make the user more comfortable using the component 104. Such recommendations may be presented to the user through a UI (e.g., in an application) executing on the user device 128. In some implementations, the configuration update(s) 126 are communicated to the component 104. The update(s) 126 are received through the network controller(s) 106 and accessed by software (e.g., firmware) executing on the processor 108, which sends instructions to the various actuator(s) 114 to adjust the subcomponents according to the configuration update(s) 126. Accordingly, the configuration update(s) 126 may be applied automatically to the component 104 without further user input. In some implementations, the user may be prompted to approve or disapprove a particular set of configuration update(s) 126 before they are applied to the component 104. In some implementations, the user may opt-in to the service to receive configuration update(s) 126 that are automatically applied to the component 104 without further permission required from the user. In each scenario, the user may be notified after the configuration update(s) 126 have been applied to the component 104.

In some implementations, the analysis of the sensor data 118, the determination of the configuration update(s) 126, the communication of the configuration update(s) 126 to the user device 128 and/or the component 104, and/or the automatic application of the configuration update(s) 126 to the component 104 may be performed in real time with respect to the generation of the sensor data 118 and/or the receipt of the sensor data 118 at the server(s) 120. As used herein, a real time operation may describe an operation that is performed based on a triggering event and without any intentional delay between the performed operation and the triggering event, taking into account network communication latency, the processing and/or communication limitations of the computing system(s) performing the operation, and the time needed to initiate and/or perform the operation. The triggering event may be a received communication (e.g., receipt of sensor data 118), a detection of a particular application state, another operation performed by the same or a different process, and so forth. A real time operation may also be described as a dynamic operation. Real time operations may include operations that are automatically executed in response to the triggering event without requiring human input at run-time. In some examples, a real time operation may be performed within a same execution path as a process that detects and/or handles the triggering event. For example, the real time operation may be performed or initiated by code that executes as part of the handling of the event and/or in response to a message that is sent as part of the handling of the event. A real time operation may, in at least some instances, be performed synchronously with respect to the triggering event.

The real time generation of the configuration update(s) 126 may provide a satisfaction improvement service that is able to respond quickly and dynamically to the perceived and/or inferred discomfort of the user using the component 104, by providing configuration update(s) 126 that are predicted to reduce the user's physical discomfort and/or otherwise enhance the usability, performance, and/or functional effectiveness of the component 104.

In some implementations, the server(s) 120 execute one or more design modules 130. The design module(s) 130 receive the sensor data 118 from various instances of a particular component 104, such as multiple instances of a same or similar car seat being used in different vehicles by different users. The design module(s) 130 may aggregate the various sets of sensor data 118 to generate aggregate sensor data. Based on the aggregate sensor data, the design module(s) 130 may generate one or more design updates 132 that include modification(s) to the design of the component 104. For example, the design update(s) 132 may add new features, remove existing features, and/or modify existing features of the component 104 to provide a design for a subsequent version of the component 104 (e.g., to be manufactured in the future). The analysis of the aggregate sensor data may be performed as batch processing, in which a period time period batch (e.g., one week of data, one month of data, etc.) is analyzed to generate the design update(s) 132. The design module(s) 130 may use the aggregate sensor data, collected for a particular component, to modify an existing design and/or create a new design for the component 104.

In some implementations, the design update(s) 132 may be determined based on a designer's input to a UI 134, such as a design view of the component 104 presented within a CAD or CAM system, or other suitable design interview for the component 104. For example, a current design of the component 104 may be presented in the design view. The presented design may be overlaid or otherwise supplemented, in the design view, with graphics showing one or more portions and/or subcomponents of the component for which the aggregate sensor data indicates one or more users performing actions described in the sensor data 118. For example, a graphic overlay may indicate those portions of the component 104 in contact with users who tend to be fidgeting, and/or those portions of the component 104 that were the target of attempted manual adjustments by users. In this way, the graphic overlay indicates those portions or subcomponents that users found to be physically uncomfortable or otherwise unsatisfactory. In some implementations the design view overlay may indicate a range of motion or other possible modifications to portions or subcomponents of the component 104, such as an available range of adjustments to a lumbar support, head support, car seat position, and so forth. In some implementations, the graphic overlay may be generated based on a ML analysis, such as clustering, to determine clusters of locations on the component where various users were performing actions relative to the component 104. A designer may use the design view, with the graphic overlays for zones of satisfaction and/or dissatisfaction, to modify the design of the component 104 and generate the design update(s) 132. Alternatively, in some implementations, a ML model may be employed to generate the design update(s) 132 automatically based on the input aggregate sensor data.

Implementations may provide configuration update(s) 126 and/or design update(s) 132 in response to conscious user actions and/or subconscious user actions. For example, the user may consciously attempt to adjust the configuration of the component 104, and such attempted adjustments may be detected and analyzed to determine a more optimal configuration of the component 104 that may be more comfortable for the user. As another example, the user may mention aloud that they are unsatisfied with the component (e.g., "this car seat is uncomfortable"), either after being prompted by the component or some other system, or without being prompted to offer such information. Conscious actions may also include gestures (e.g., pointing to the component, hitting the component, etc.).

Unconscious actions may include fidgeting and/or other types of movements (or other actions) that the user may be unaware of performing. Such unconscious activities may also be detected and analyzed to determine a more optimal configuration that may be more comfortable and/or that may reduce the user's fidgeting. Other biometric characteristics of the user may also be monitored and used to infer discomfort, such as the user's body temperature, perspiration level, pulse, respiration rate, and so forth. In some implementations, a detected deviation of the user from their normal behavior with respect to the component may be also be used to generate the configuration update(s) 126 and/or design update(s) 132. For example, a detected increase in the frequency of the user pumping the brakes on a vehicle or revving its engine may be used to generate updated configuration and/or design information for an engine component or subcomponent.

In some implementations, timing is a factor in determining the configuration update(s) 126 and/or design update(s) 132 to the component 104. For example, recommendations for configuration updates may be generated quickly within a period of time after the user has started using the component, such that the recommendations may be provided before the user has had time to become acclimated to a possibly sub-optimal configuration of the component. In some instances, configuration updates may be generated based on at least a minimum time period of collected sensor data, to avoid making recommendations too quickly based on the initial (e.g., transient and possible changeable) state of interaction of the user with the component.

In some implementations, the analysis to determine the configuration update(s) and/or design update(s) 132 may also take into account logs that describe a history of the user interaction with the component, such as a history of past configuration settings, historical sensor data, logs describing usage patterns of the component by one or more users, and so forth. Environmental factors, such as ambient temperature, air pressure, humidity, wind speed, ambient light level, ambient sound level, and so forth may also be used to determine configuration update(s) 126 and/or design update(s) 132. In some instances, recommendations for configuration updates may also take into account a type of use of the component 104. For example, different configurations may be recommended for a car seat based on whether the user is currently on a short drive or a long drive. The configuration updates and/or design updates may also be based on determined characteristics of the user of the component, such as the user's height, weight, age, and so forth. Such user characteristics may be measured by one or more of the sensor(s), and/or may be previously determined for the user and stored in a user profile.

Figure 2:
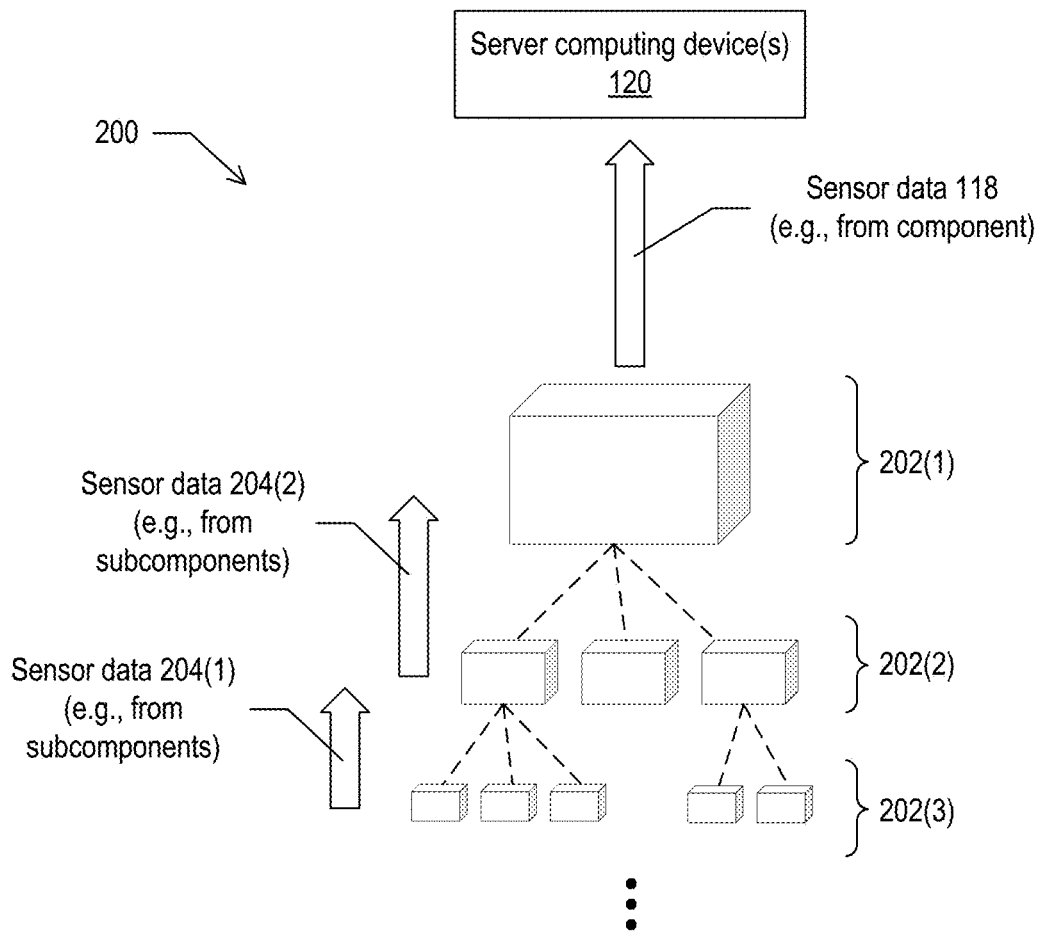
FIG. 2 depicts an example of a component hierarchy for sensor data generation and collection, according to implementations of the present disclosure.

FIG. 2 depicts an example of a component hierarchy 200 for sensor data generation and collection, according to implementations of the present disclosure. In some implementations, the various components 104 of a system under diagnosis 102 may be logically organized in a hierarchy, with certain components including subcomponents, which can include their own subcomponents, and so forth. In the example show, the components include a top-level component 202(1), which includes various subcomponents 202(2), each of which may include any number of its own subcomponents 202(3), and so forth. The hierarchy may include any suitable number of levels of subcomponents. In some implementations, the sensor data 204(1) generated from one level of subcomponents may be communicated to the parent component(s), which may communicate the accumulated sensor data 204(2) up to the next level, until the top-level component 202(1) communicates the accumulated sensor data from the entire tree to the server(s) 120.

In some implementations, in the hierarchical arrangement of components, each component may operate as its own platform with its own computing capabilities, storage, and/or other resources (e.g., as a computing device). Accordingly, each component may individually determine its own satisfaction metric based on its analyzed sensor data, and the determined satisfaction metric may be propagated upward in the hierarchy and communicated to the server(s) 120. In some instances, the satisfaction metric at a particular component level may be based, at least in part, on the satisfaction levels determined at the components at lower levels in the hierarchy.

In one example, where the system under diagnosis 102 is a vehicle, a component may include a car seat which has its own sensors, actuators, processing capacity, and so forth. The car seat may include subcomponents such as a lumbar support, head support, and so forth. Each of these subcomponents may include its own subcomponents, and so forth. Sensor data may be analyzed, and a satisfaction metric may be determined, based on a particular component at any level in the hierarchy and/or based on the accumulated satisfaction metrics of the hierarchy.

Figure 3:
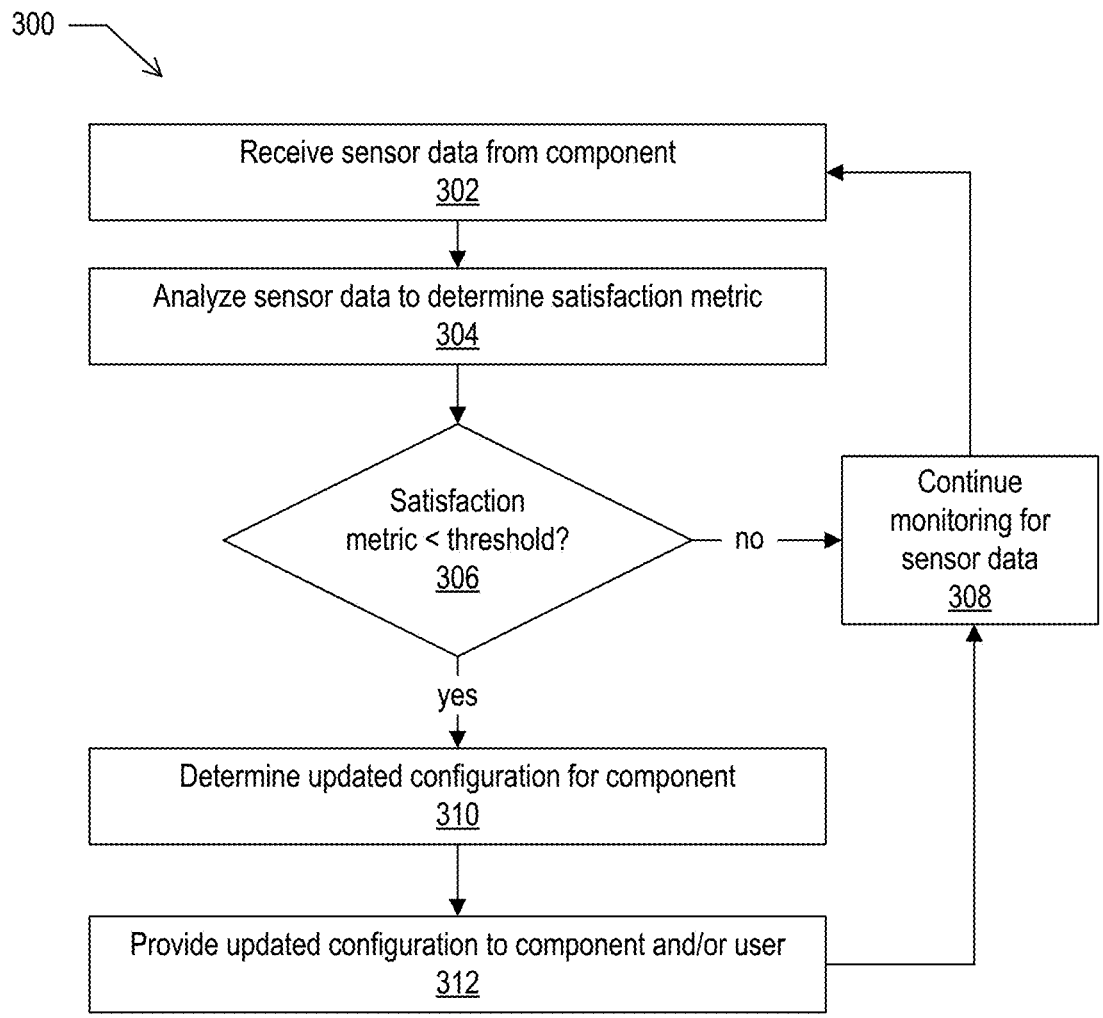
FIG. 3 depicts a flow diagram of an example process for component configuration, according to implementations of the present disclosure.

FIG. 3 depicts a flow diagram 300 of an example process for component configuration, according to implementations of the present disclosure. Operations of the process can be performed by one or more of the API 122, the user satisfaction module(s) 124, the design module(s) 130, the UI 134, and/or other software module(s) executing on the server(s) 120, the component(s) 104, the user device 128, or elsewhere.

The sensor data 118 is received (302) from a component 104. The sensor data 118 may describe a current state of the component 104, a current state of the user using the component 104 (e.g., physiological state), the environment in proximity to the component 104, and/or one or more actions (e.g., movements, gestures, comments, etc.) performed by the user while using the component 104 in its current configuration. Information describing the current configuration (e.g., currently settings) of the component 104 may also be received. The sensor data 118 may be analyzed (304) to determine a satisfaction metric that indicates a level of satisfaction of the user in the current configuration of the component 104. A determination may be made (306) whether the satisfaction metric is below a predetermined threshold level. If not, the system may continue monitoring (308) for sensor data 118 that indicates user dissatisfaction. If the satisfaction level is below the threshold, the sensor data 118 may be analyzed to determine (310) configuration updates for the component, as described above. The configuration update(s) may be generated to increase the level of satisfaction of the user in the component, and/or may be predicted to increase the level of satisfaction. The configuration updates may be provided (312) the component 104 (e.g., for automatic activation) and/or to the user (e.g., as recommended settings). The system may then continue monitoring (308). As described above, in some implementations, the analysis of the sensor data 118 may be performed in real time with respect to the generation and/or receipt of the sensor data 118.

Figure 4:
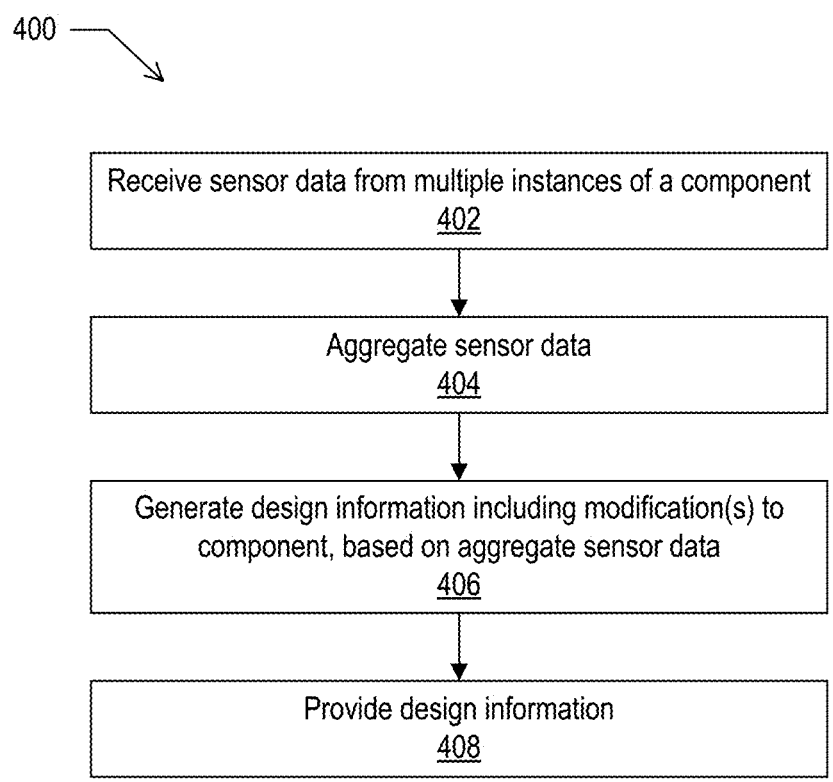
FIG. 4 depicts a flow diagram of an example process for component design, according to implementations of the present disclosure.

FIG. 4 depicts a flow diagram 400 of an example process for component design, according to implementations of the present disclosure. Operations of the process can be performed by one or more of the API 122, the user satisfaction module(s) 124, the design module(s) 130, the UI 134, and/or other software module(s) executing on the server(s) 120, the component(s) 104, the user device 128, or elsewhere.

Sensor data 118 is received (402) from multiple instances of a component 104 being used by various users. The sensor data 118 may be aggregated (404). In some implementations, the aggregation may employ a clustering algorithm that identifies particular actions that are more frequently performed by users of the components 104 compared to other actions, and/or particular portions (or subcomponents) of the component 104 that are more likely to be the subject of such actions than other portions (or subcomponents). The aggregate sensor data is employed to generate (406) design information that includes one or more modifications to the component, as described above. The design information is provided (408) for presentation through a user interface. In some implementations, the design information may be provided to a manufacturing automation system to begin manufacturing a next version of the component 104 based on the design information.

Figure 5:
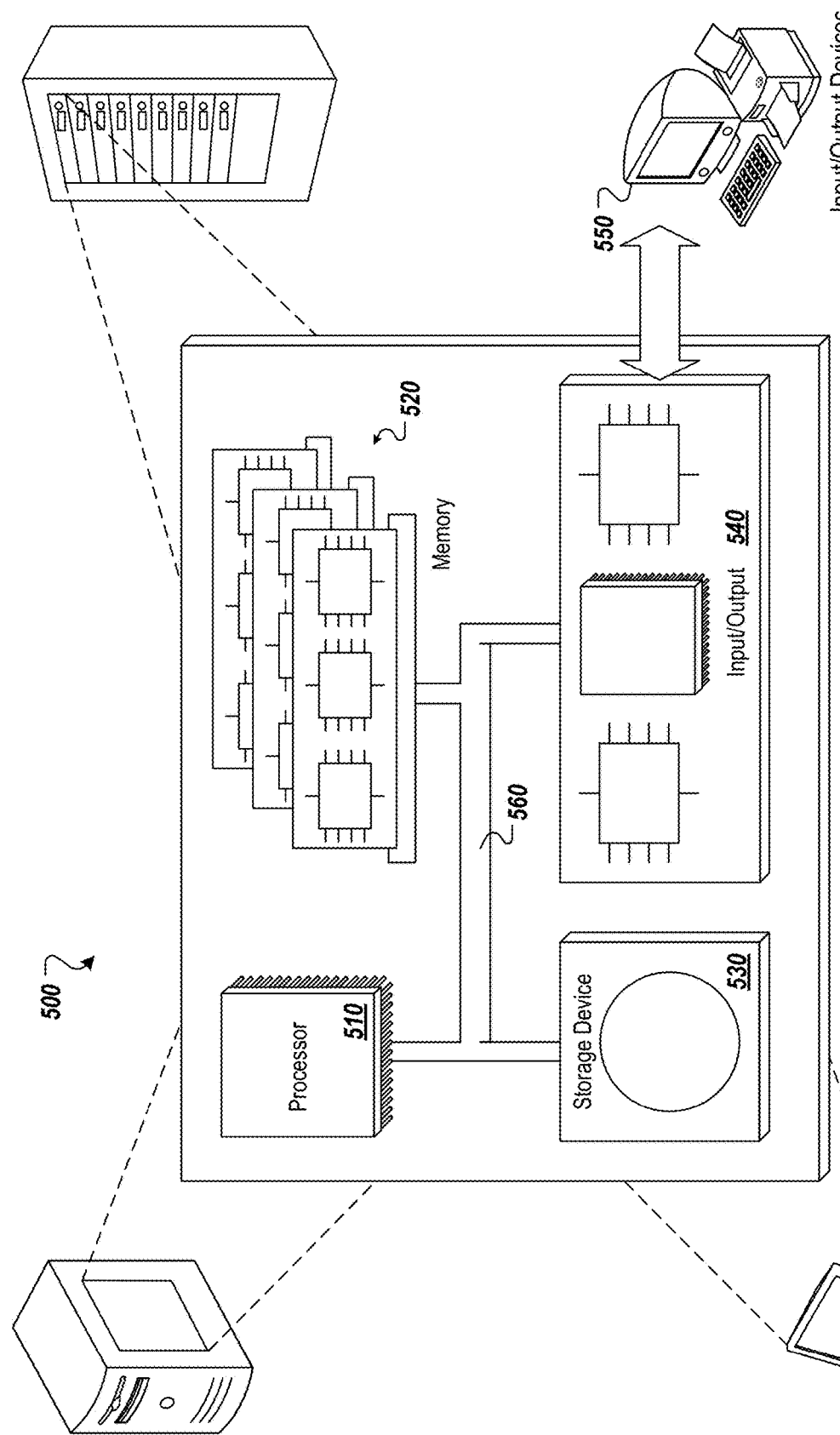
FIG. 5 depicts an example computing system, according to implementations of the present disclosure.

FIG. 5 depicts an example computing system 500, according to implementations of the present disclosure. The system 500 may be used for any of the operations described with respect to the various implementations discussed herein. For example, the system 500 may be included, at least in part, in one or more of the system under diagnosis 102, the component(s) 104, the server computing device(s) 120, the user device 128, and/or other computing device(s) or system(s) described herein. The system 500 may include one or more processors 510, a memory 520, one or more storage devices 530, and one or more input/output (I/O) devices 550 controllable via one or more I/O interfaces 540. The various components 510, 520, 530, 540, or 550 may be interconnected via at least one system bus 560, which may enable the transfer of data between the various modules and components of the system 500.

The processor(s) 510 may be configured to process instructions for execution within the system 500. The processor(s) 510 may include single-threaded processor(s), multi-threaded processor(s), or both. The processor(s) 510 may be configured to process instructions stored in the memory 520 or on the storage device(s) 530. For example, the processor(s) 510 may execute instructions for the various software module(s) described herein. The processor(s) 510 may include hardware-based processor(s) each including one or more cores. The processor(s) 510 may include general purpose processor(s), special purpose processor(s), or both.

The memory 520 may store information within the system 500. In some implementations, the memory 520 includes one or more computer-readable media. The memory 520 may include any number of volatile memory units, any number of non-volatile memory units, or both volatile and non-volatile memory units. The memory 520 may include read-only memory, random access memory, or both. In some examples, the memory 520 may be employed as active or physical memory by one or more executing software modules.

The storage device(s) 530 may be configured to provide (e.g., persistent) mass storage for the system 500. In some implementations, the storage device(s) 530 may include one or more computer-readable media. For example, the storage device(s) 530 may include a floppy disk device, a hard disk device, an optical disk device, or a tape device. The storage device(s) 530 may include read-only memory, random access memory, or both. The storage device(s) 530 may include one or more of an internal hard drive, an external hard drive, or a removable drive.

One or both of the memory 520 or the storage device(s) 530 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 500. In some implementations, the CRSM may include a data store that provides storage of computer-readable instructions or other information in a non-transitory format. The CRSM may be incorporated into the system 500 or may be external with respect to the system 500. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 510 and the memory 520 may be supplemented by, or incorporated into, one or more application-specific integrated circuits (ASICs).

The system 500 may include one or more I/O devices 550. The I/O device(s) 550 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 550 may also include one or more output devices such as a display, LED(s), an audio output device (e.g., a speaker), a printer, a haptic output device, and so forth. The I/O device(s) 550 may be physically incorporated in one or more computing devices of the system 500, or may be external with respect to one or more computing devices of the system 500.

The system 500 may include one or more I/O interfaces 540 to enable components or modules of the system 500 to control, interface with, or otherwise communicate with the I/O device(s) 550. The I/O interface(s) 540 may enable information to be transferred in or out of the system 500, or between components of the system 500, through serial communication, parallel communication, or other types of communication. For example, the I/O interface(s) 540 may comply with a version of the RS-232 standard for serial ports, or with a version of the IEEE 1284 standard for parallel ports. As another example, the I/O interface(s) 540 may be configured to provide a connection over Universal Serial Bus (USB) or Ethernet. In some examples, the I/O interface(s) 540 may be configured to provide a serial connection that is compliant with a version of the IEEE 1394 standard.

The I/O interface(s) 540 may also include one or more network interfaces that enable communications between computing devices in the system 500, or between the system 500 and other network-connected computing systems. The network interface(s) may include one or more network interface controllers (NICs) or other types of transceiver devices configured to send and receive communications over one or more communication networks using any network protocol.

Computing devices of the system 500 may communicate with one another, or with other computing devices, using one or more communication networks. Such communication networks may include public networks such as the internet, private networks such as an institutional or personal intranet, or any combination of private and public networks. The communication networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 500 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor may receive instructions and data from a read only memory or a random access memory or both. Elements of a computer can include a processor for performing instructions and one or more memory devices for storing instructions and data. Generally, a computer may also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS)

receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claim(s).

The invention claimed is:

1. A system comprising:
    at least one processor; and
    a memory communicatively coupled to the at least one processor, the memory storing instructions which, when executed by the at least one processor, cause the at least one processor to perform operations comprising:
    receiving first sensor data describing at least one adjustment to a vehicle component that a user is using, that the user has made to improve the user's comfort in using the vehicle component;
    after the user has made the adjustment to the vehicle component, receiving second sensor data that is other than data that reflects an explicit input, by the user, that the adjustment to the vehicle component failed to adequately improve the user's comfort in using the vehicle component, then automatically determining, based on the second sensor data, that the adjustment to the vehicle component likely failed to adequately improve the user's comfort in using the vehicle component;
    in response to automatically determining that the adjustment to the vehicle component likely failed to adequately improve the user's comfort in using the vehicle component, providing, to a machine learning-trained model that is trained based on adjustments to similar vehicle components by other users, to output additional adjustments to the vehicle component that can be automatically made to improve users' comfort in using the vehicle component, (i) the first sensor data and (ii) data indicating a current state of the adjusted vehicle component;
    receiving, from the machine learning-trained model, an additional adjustment that can be automatically made to improve the user's comfort in using the vehicle component; and
    communicating the additional adjustment to the vehicle component.

2. The system of claim 1, wherein determining that the adjustment failed to adequately improve the user's comfort comprises determining that the user is fidgeting while using the vehicle component.

3. The system of claim 1, wherein determining that the adjustment failed to adequately improve the user's comfort comprises determining that the user has made one or more additional adjustments to the vehicle component.

4. The system of claim 1, wherein the first sensor data is generated by one or more sensors inside of the vehicle component, and the second sensor data is generated by one or more sensors that are external to the vehicle component.

5. The system of claim 1, wherein the operations comprise prompting the user with information regarding the additional adjustment contemporaneously with communicating the additional adjustment to the vehicle component.

6. The system of claim 1, wherein the operations comprise determining an estimated height or weight of the user, wherein the estimated height or weight are provided to the machine learning-trained model.

7. The system of claim 1, wherein the second sensor data comprise audio data comprising an utterance that was directed at another passenger of the vehicle.

8. A computer-implemented method comprising:
receiving, by one or more processors, first sensor data describing at least one adjustment to a vehicle component that a user is using, that the user has made to improve the user's comfort in using the vehicle component;
after the user has made the adjustment to the vehicle component, receiving, by the one or more processors, second sensor data that is other than data that reflects an explicit input, by the user, that the adjustment to the vehicle component failed to adequately improve the user's comfort in using the vehicle component, then automatically determining, based on the second sensor data, that the adjustment to the vehicle component likely failed to adequately improve the user's comfort in using the vehicle component;
in response to automatically determining that the adjustment to the vehicle component likely failed to adequately improve the user's comfort in using the vehicle component, providing, by the one or more processors and to a machine learning-trained model that is trained based on adjustments to similar vehicle components by other users, to output additional adjustments to the vehicle component that can be automatically made to improve users' comfort in using the vehicle component, (i) the first sensor data and (ii) data indicating a current state of the adjusted vehicle component;
receiving, by the one or more processors and from the machine learning-trained model, an additional adjustment that can be automatically made to improve the user's comfort in using the vehicle component; and
communicating, by the one or more processors, the additional adjustment to the vehicle component.

9. The method of claim 8, wherein determining that the adjustment failed to adequately improve the user's comfort comprises determining that the user is fidgeting while using the vehicle component.

10. The method of claim 8, wherein determining that the adjustment failed to adequately improve the user's comfort comprises determining that the user has made one or more additional adjustments to the vehicle component.

11. The method of claim 8, wherein the first sensor data is generated by one or more sensors inside of the vehicle component, and the second sensor data is generated by one or more sensors that are external to the vehicle component.

12. The method of claim 8, comprising prompting the user with information regarding the additional adjustment contemporaneously with communicating the additional adjustment to the vehicle component.

13. The method of claim 8, comprising determining an estimated height or weight of the user, wherein the estimated height or weight are provided to the machine learning-trained model.

14. The method of claim 8, wherein the second sensor data comprise audio data comprising an utterance that was directed at another passenger of the vehicle.

15. A non-transitory computer-readable storage medium storing instructions which, when executed by at least one processor, cause the at least one processor to perform operations comprising:
receiving first sensor data describing at least one adjustment to a vehicle component that a user is using, that the user has made to improve the user's comfort in using the vehicle component;
after the user has made the adjustment to the vehicle component, receiving second sensor data that is other than data that reflects an explicit input, by the user, that the adjustment to the vehicle component failed to adequately improve the user's comfort in using the vehicle component, then automatically determining, based on the second sensor data, that the adjustment to the vehicle component likely failed to adequately improve the user's comfort in using the vehicle component;
in response to automatically determining that the adjustment to the vehicle component likely failed to adequately improve the user's comfort in using the vehicle component, providing, to a machine learning-trained model that is trained based on adjustments to similar vehicle components by other users, to output additional adjustments to the vehicle component that can be automatically made to improve users' comfort in using the vehicle component, (i) the first sensor data and (ii) data indicating a current state of the adjusted vehicle component;
receiving, from the machine learning-trained model, an additional adjustment that can be automatically made to improve the user's comfort in using the vehicle component; and
communicating the additional adjustment to the vehicle component.

16. The medium of claim 15, wherein determining that the adjustment failed to adequately improve the user's comfort comprises determining that the user is fidgeting while using the vehicle component.

17. The medium of claim 15, wherein determining that the adjustment failed to adequately improve the user's comfort comprises determining that the user has made one or more additional adjustments to the vehicle component.

18. The medium of claim 15, wherein the first sensor data is generated by one or more sensors inside of the vehicle component, and the second sensor data is generated by one or more sensors that are external to the vehicle component.

19. The medium of claim 15, wherein the operations comprise prompting the user with information regarding the additional adjustment contemporaneously with communicating the additional adjustment to the vehicle component.

20. The medium of claim 15, wherein the operations comprise determining an estimated height or weight of the user, wherein the estimated height or weight are provided to the machine learning-trained model.

21. The medium of claim 15, wherein the second sensor data comprise audio data comprising an utterance that was directed at another passenger of the vehicle.

* * * * *